(12) United States Patent
Han et al.

(10) Patent No.: US 12,624,699 B2
(45) Date of Patent: May 12, 2026

(54) MAGNETIC LEVITATION CENTRIFUGAL PUMP

(71) Applicant: ROCKETHEART TECHNOLOGY CO. LTD, Tianjin (CN)

(72) Inventors: Zhifu Han, Tianjin (CN); Wenjin Wu, Tianjin (CN); Qinglin Fan, Tianjin (CN); Xuman Zhang, Tianjin (CN); Ying Dai, Tianjin (CN); Pengfei Jing, Tianjin (CN); Guogang Song, Tianjin (CN)

(73) Assignee: ROCKETHEART TECHNOLOGY CO. LTD, Tianjin (CN)

( * ) Notice: Subject to any disclaimer, the term of this patent is extended or adjusted under 35 U.S.C. 154(b) by 0 days.

(21) Appl. No.: 18/866,965

(22) PCT Filed: May 22, 2023

(86) PCT No.: PCT/CN2023/095453
§ 371 (c)(1),
(2) Date: Nov. 18, 2024

(87) PCT Pub. No.: WO2023/226916
PCT Pub. Date: Nov. 30, 2023

(65) Prior Publication Data
US 2025/0327454 A1 Oct. 23, 2025

(30) Foreign Application Priority Data

May 23, 2022 (CN) .......................... 202210565532.4

(51) Int. Cl.
| | |
|---|---|
| *F04D 13/06* | (2006.01) |
| *A61M 60/232* | (2021.01) |
| *A61M 60/422* | (2021.01) |
| *A61M 60/82* | (2021.01) |
| *F04D 13/02* | (2006.01) |

(52) U.S. Cl.
CPC ......... *F04D 13/064* (2013.01); *F04D 13/026* (2013.01); *F04D 13/027* (2013.01);
(Continued)

(58) Field of Classification Search
CPC .. A61M 60/422; A61M 60/232; A61M 60/82; A61M 60/804; F04D 13/0666; F04D 13/066; F04D 13/064
See application file for complete search history.

(56) References Cited

U.S. PATENT DOCUMENTS

| | | | |
|---|---|---|---|
| 6,227,817 B1 | 5/2001 | Paden | |
| 2003/0091450 A1* | 5/2003 | Davis .................. | A61M 60/237 |
| | | | 417/423.7 |

(Continued)

FOREIGN PATENT DOCUMENTS

| | | |
|---|---|---|
| CN | 102247628 A | 11/2011 |
| CN | 113082506 A | 7/2021 |

(Continued)

OTHER PUBLICATIONS

International Search Report dated Sep. 28, 2023 issued in PCT/CN2023/095453.

(Continued)

*Primary Examiner* — Kenneth J Hansen
(74) *Attorney, Agent, or Firm* — Scully, Scott, Murphy & Presser, P.C.

(57) ABSTRACT

A magnetic levitation centrifugal pump, including a volute, stator magnetic ring and a rotor; the volute has a levitation cavity, a medium inlet and a medium outlet, the rotor is located inside the levitation cavity, the stator magnetic ring are fixed to the volute, and the rotor includes a rotor body and dynamic magnetic ring located on the rotor body; the dynamic magnetic ring and the stator magnetic ring are coaxial with each other and are nested, to limit the radial
(Continued)

positions of the rotor body and the volute; magnet steel assemblies are further fixed at the rotor body, each magnet steel assembly includes N first magnet steels arranged along the circumferential direction, and magnetic poles of all the first magnet steels are arranged in a staggered manner; two ends of the volute are also encapsulated with driving coil assemblies.

11 Claims, 11 Drawing Sheets

(52) U.S. Cl.
CPC ......... *A61M 60/232* (2021.01); *A61M 60/422* (2021.01); *A61M 60/82* (2021.01)

(56) References Cited

U.S. PATENT DOCUMENTS

| | | | |
|---|---|---|---|
| 2012/0035411 A1 | 2/2012 | Larose et al. | |
| 2014/0205467 A1 | 7/2014 | Yanai et al. | |
| 2016/0131141 A1 | 5/2016 | Sato et al. | |
| 2016/0281728 A1 | 9/2016 | Ozaki et al. | |
| 2018/0010608 A1* | 1/2018 | Larose | F04D 7/04 |
| 2023/0208227 A1* | 6/2023 | Zhou | F04D 29/20 |
| | | | 417/423.7 |

FOREIGN PATENT DOCUMENTS

| | | | |
|---|---|---|---|
| CN | 217938905 U | 12/2022 | |
| EP | 3173109 A1 | 5/2017 | |
| JP | 2007089972 A | 4/2007 | |
| JP | 2009523488 A | 6/2009 | |
| WO | 2016158173 A1 | 10/2016 | |

OTHER PUBLICATIONS

Extend European search report dated Mar. 14, 2025 received in European Patent Application No. 23810987.0.

The First Office Action of counterpart JP application No. 2024-572604 was issued on Nov. 18, 2025.

* cited by examiner

1212

100a

100a

1212

MAGNETIC LEVITATION CENTRIFUGAL PUMP

CROSS-REFERENCE TO RELATED APPLICATION

The present disclosure claims priority to Chinese Patent Application No. 202210565532.4, filed to the China National Intellectual Property Administration on May 23, 2022 and entitled "Magnetic levitation centrifugal pump", which is incorporated herein by reference in its entirety.

TECHNICAL FIELD

The present disclosure relates to the technical field of vibration damping, and in particular, to a magnetic levitation centrifugal pump.

BACKGROUND

Heart failure, popular speaking, is a failure that a natural heart cannot pump sufficient blood flow to maintain systemic blood circulation. Statistics of the World Health Organization (WTO) show that approximately 15%-20% of people suffer from varying degrees of heart failure, the number of people aged 65 or older who are hospitalized due to heart failure accounts for 50% or more of all hospitalizations, while the case fatality rate after 5 years exceeds 50%. For heart failure patients, there are only three therapy pathways: conservative drug therapy, heart transplantation and ventricular assist. The effect of drug therapy is poor, and heart transplantation is very difficult due to the limitation of donors, so a Ventricular Assist Device (VAD) becomes the most effective treatment pathway for all types of end-stage heart failures recognized all over the world. A main component of the ventricular assist device is a blood pump. Generally, an inflow pipeline of the blood pump is connected with a left ventricle or a right ventricle of a human heart, and an outflow pipeline is connected with an aorta or a pulmonary artery. The pump is connected with a control driver (provided with a power supply apparatus); and the control driver controls the blood pump to output blood with a certain pressure (generally in a range of 80-120 mmHg) and flow (generally in a range of 2-10 L/min), so as to share the power demand of the human heart for normal human activities.

In view of the limitation of use environment of the blood pump, on the premise of satisfying functions, how to enable the blood pump to have the characteristics of high integration and small volume is a technical problem always concerned by those skilled in the art.

SUMMARY

An object of some embodiments of the present disclosure is to provide a magnetic levitation centrifugal pump having a small volume and a compact structure.

Some embodiments of the present disclosure provide a magnetic levitation centrifugal pump, including a volute, stator magnetic ring and a rotor;

the volute is provided with a levitation cavity, a medium inlet and a medium outlet, the rotor is located inside the levitation cavity, and the stator magnetic ring is fixed to the volute;

the rotor includes a rotor body and a dynamic magnetic ring positioned on the rotor body; the dynamic magnetic ring and the stator magnetic ring are coaxial with each other and are nested, to limit radial positions of the rotor body and the volute;

a magnet steel assembly is further fixed at the rotor body, the magnet steel assembly includes N first magnet steels arranged along a circumferential direction, and magnetic poles of all the first magnet steels are arranged alternately;

two ends of the volute are also encapsulated with driving coil assemblies, and the two driving coil assemblies cooperate with the magnet steel assembly to provide an axial force for the rotor body to move in an axial direction and a rotational force for the rotor body to move axially.

In the centrifugal pump provided in some embodiments of the present disclosure, axial limiting is provided by the magnet steel assemblies arranged at two ends of the rotor body and corresponding driving coil assemblies on the volute; no additional coil and sensor assembly is required, and thus no additional power consumption is generated due to position control. Since a sensor assembly is not required for axial position control, the centrifugal pump implanted into the body has no electronic device, has a stronger anti-interference capability, higher reliability, and does not decrease in performance with an increase of working time. Therefore, compared with the related art, this axial levitation technique is able to achieve high reliability and miniaturization of a blood pump.

In addition, in some embodiments of the present disclosure, full levitation operation of the rotor is able to be realized by the magnetic action between the dynamic magnetic ring and the stator magnetic ring; in this way, there is no mechanical contact between the rotor and the volute (equivalent to a stator), thereby reducing the heat generated and wear, and maximally reducing a possibility of thrombus generation and crushing damage to blood cells. A radial levitation limit of the rotor is able to be realized by the dynamic magnetic ring and the stator magnetic ring.

In some embodiments, two ends of the rotor body are both provided with the magnet steel assembly, and the magnet steel assemblies at the two ends of the rotor body are symmetrical with respect to a central cross section of the rotor body; the driving coil assemblies located at the two ends of the volute are symmetrical with respect to a central cross section of the levitation cavity; one of the two magnet steel assemblies and one of the two driving coil assemblies at a same side form a disc-type motor, and disc-type motors at the two ends jointly provide the axial force for the rotor body to move in the axial direction and the rotational force for the rotor body to move in the axial direction;

or/and adjacent first magnet steels are closely attached, or the magnet steel assembly further includes transverse magnetic conductive magnet steels, the magnetic conductive magnet steels being located between two first magnet steels, and all the magnetic conductive magnet steels and all the first magnet steels form an Halbach magnet steel array.

In some embodiments, at least one end of the rotor body is also encapsulated with a magnetic component, corresponding end of the volute is also encapsulated with a magnetic levitation coil, and when the magnetic levitation coil is energized, the magnetic levitation coil and the magnetic component generate an axial force; wherein the magnetic component includes at least one of an iron core or a second magnet steel.

In some embodiments, the two ends of the rotor body are both encapsulated with the magnetic components, and two magnetic components are able to be symmetrical with respect to a central cross section of the rotor body; and the two ends of the volute are both encapsulated with the magnetic levitation coils, and the two magnetic levitation coils are symmetrical with respect to a central cross section of the levitation cavity.

In some embodiments, there are a plurality of magnetic components evenly arranged along the circumferential direction, and each of the plurality of magnetic components is arranged between adjacent first magnet steels;

or/and, the plurality of magnetic components and the first magnet steels are stacked in the axial direction;

or/and, the plurality of magnetic levitation coils and the driving coil assemblies are stacked in the axial direction.

In some embodiments, an inner cavity of the volute is provided with annular housings, sealed cavities are enclosed by the annular housings and the volute, and the driving coil assemblies are located in the sealed cavities; and the levitation cavity is formed between two annular housings at two ends, the two annular housings are of ceramic structures, and the driving coil assemblies are arranged abutting against the annular housings.

In some embodiments, the rotor body includes an annular body and a base body, which are fixedly connected with each other in the axial direction; liquid outlets are provided between the annular body and the base body, a central through-hole of the annular body is in communication with the liquid outlets; the central through-hole is coaxial with the medium inlet, blades are provided between the annular body and the base body to form a fully-enclosed rotor structure, and the magnet steel assemblies are encapsulated in both the annular body and the base body, and the dynamic magnetic ring is encapsulated inside the base body.

In some embodiments, the base body is provided with a first annular encapsulating cavity, the dynamic magnetic ring is nested in an inner ring wall of the first annular encapsulating cavity, first iron cores and the magnet steel assemblies encapsulated in the base body are located on the periphery of the dynamic magnetic ring; and along a radial direction, an axial height of a middle region of the first annular encapsulating cavity is greater than an axial height of an edge region of the first annular encapsulating cavity.

In some embodiments, the centrifugal pump further includes a base and a cover body, the cover body includes a cylinder provided with an opening at one end and a flow guide cone connected with the other end of the cylinder, and the opening of the cylinder is circumferentially sealed and fastened to the base; the stator magnetic ring is fixed to base by a threaded component and located inside the cylinder, and the base is in a threaded and sealed connection with the volute and coaxial with the medium inlet, and the flow guide cone passes through a central hole of the first annular encapsulating cavity and protrudes towards the medium inlet.

In some embodiments, a first auxiliary channel is formed between an outer peripheral wall and an outer end wall of the annular body and a corresponding inner wall of the volute; and a second auxiliary channel is formed between an outer peripheral wall and an outer end wall of the first annular encapsulating cavity and a corresponding inner wall of the volute, and between an inner peripheral wall of the first annular encapsulating cavity and the cover body; moreover, an outer end face of the annular body and an outer end face of the base body both have a predetermined included angle with a horizontal plane, and from outside to inside, a distance between the outer end face and the horizontal plane increases.

In some embodiments, an outer end face of the annular body and an outer end face of the base body are both provided with a plurality of protrusions; each of the plurality of protrusions extends from an inner edge side to an outer edge side, and have a predetermined included angle with a radial direction, wherein the closer to the inner edge side, the smaller a distance between adjacent protrusions, or the closer to the inner edge, the lower a height of each of the plurality of protrusions.

or/and, the blades are backward bent blades.

In some embodiments, the rotor body is an annular housing, a number of the magnet steel assembly is one, and each of the first magnet steels is encapsulated in an inner cavity of the annular housing, and each of the first magnet steels extends from one end of the rotor body to the other end; an end face of the annular housing facing towards the medium inlet of the volute is further provided with at least two groove bodies, and openings of the groove bodies face towards the medium inlet of the volute, each of the groove bodies is located between adjacent first magnet steels, and the groove bodies form main liquid flow channels of the rotor body.

BRIEF DESCRIPTION OF THE DRAWINGS

In FIGS. 1-11:

100. Rotor; 11. Base body; 111. Lower cover plate; 112. First annular encapsulating cavity; 113. Inner peripheral wall; 12. Annular body; 121. Upper cover plate; 1211. Outer end face; 1212. Protrusion; 13. Blade; 14. magnet steel assembly; 15. Magnetic component; 16. Dynamic magnetic ring; 18. Magnetic conductive magnet steel;

100'. Rotor; 141. First magnet steel; 110. Annular housing; 120. Groove body; 111'. Cover plate;

200. Volute; 201. First volute; 202. Second volute; 203. First annular housing; 204. Second annular housing; 21. Driving coil assembly; 211. Driving coil; 212. Working iron core; 22. Stator magnetic ring; 23. Base; 24. Flow guide cone; 25. Magnetic levitation coil;

300. Inlet pipe;
400. Outlet pipe;
1*a*. First auxiliary channel; 1*b*. Second auxiliary channel;
    100*a*. Liquid outlet.

DETAILED DESCRIPTION OF THE EMBODIMENTS

In the illustration of some embodiments of the present disclosure, it should be noted that orientation or positional relationships indicated by terms such as "left", "right", "upper", "lower", "inner", "outer", etc. are orientation or positional relationships based on the accompanying drawings, are only used to facilitate conciseness of the illustration of techniques, rather than indicating or implying that a device or element referred to must have a specific orientation, and be constructed and operated in the specific orientation, and therefore said terms cannot be understood as limitation to some embodiments of the present disclosure. In addition, terms such as "first" and "second", etc. are only used to facilitate illustration of two or more structures or components that are identical or similar in structure and/or function, and do not represent certain specific limitations to the sequence and/or importance.

Without loss of generality, technical solutions and technical effects are introduced herein by taking a magnetic levitation centrifugal pump being applied to a heart pumping blood as an example. A person skilled in the art should understand that for the magnetic levitation centrifugal pump according to some embodiments of the present disclosure, the technical solutions are proposed on the basis of studying a blood pump, but the magnetic levitation centrifugal pump herein is not limited to be applied to a heart pumping blood, and applications of said centrifugal pump to other fields are still within the scope of protection of the present disclosure.

To make a person skilled in the art better understand the technical solutions of some embodiments of the present disclosure, hereinafter, some embodiments of the present disclosure are further described in detail with reference to the accompanying drawings and specific embodiments.

Figure 1:
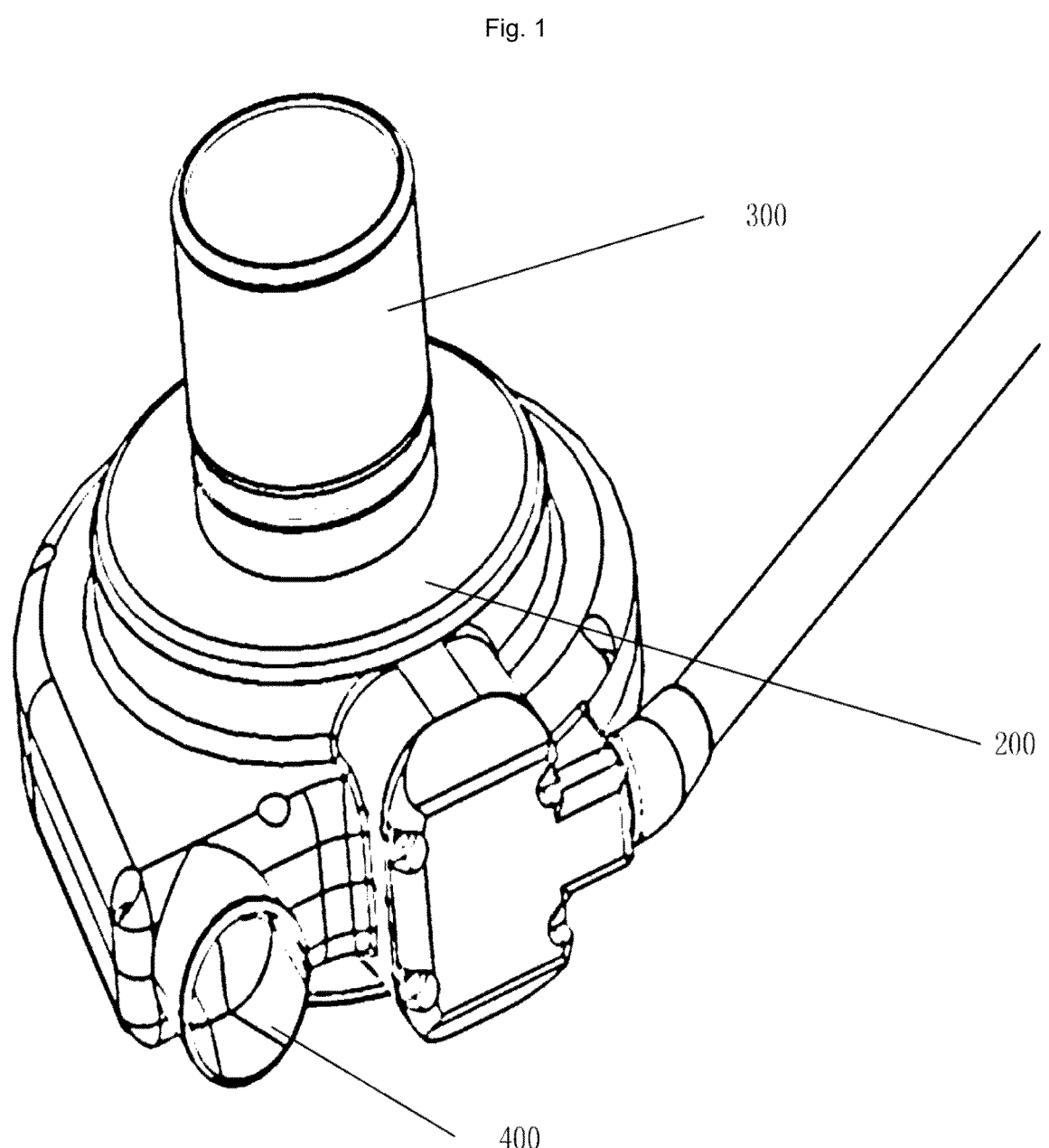
FIG. 1 is a schematic diagram of a three-dimensional structure of a magnetic levitation centrifugal pump according to some embodiments of the present disclosure.
Figure 2:
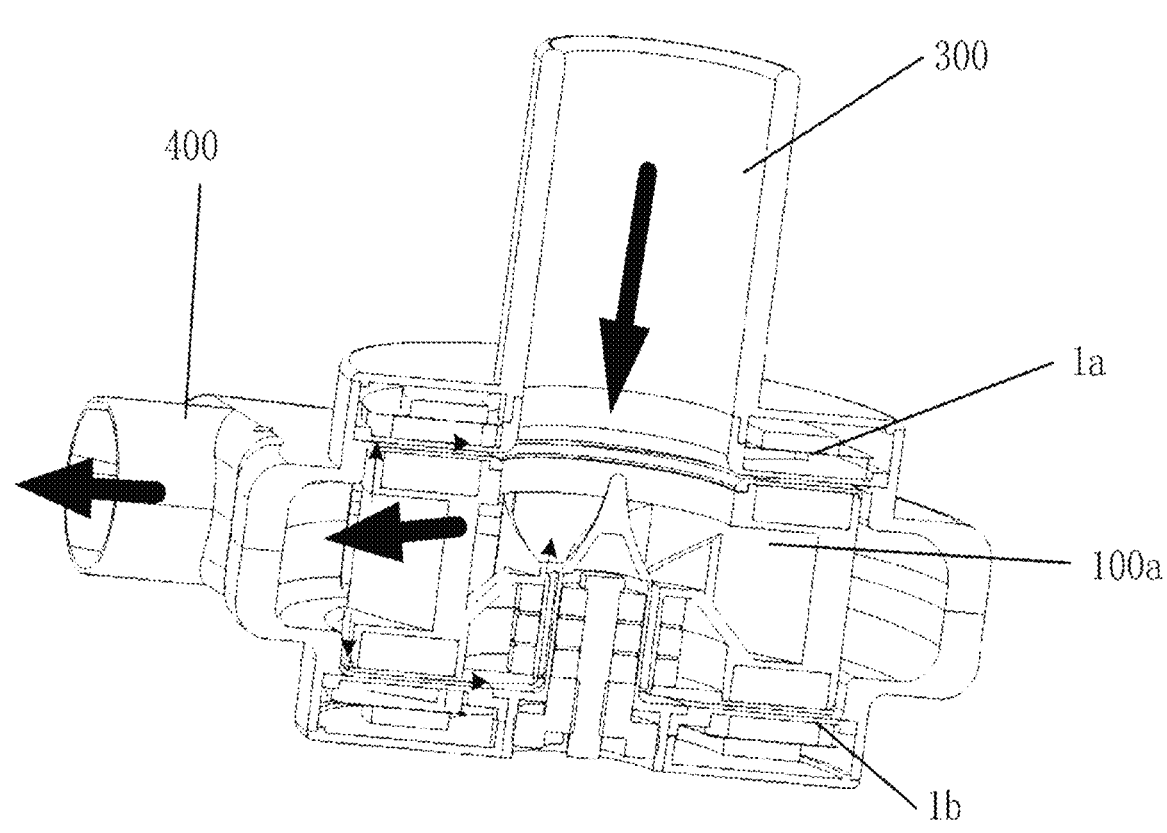
FIG. 2 is a cross-sectional three-dimensional view of a magnetic levitation centrifugal pump.
Figure 3:
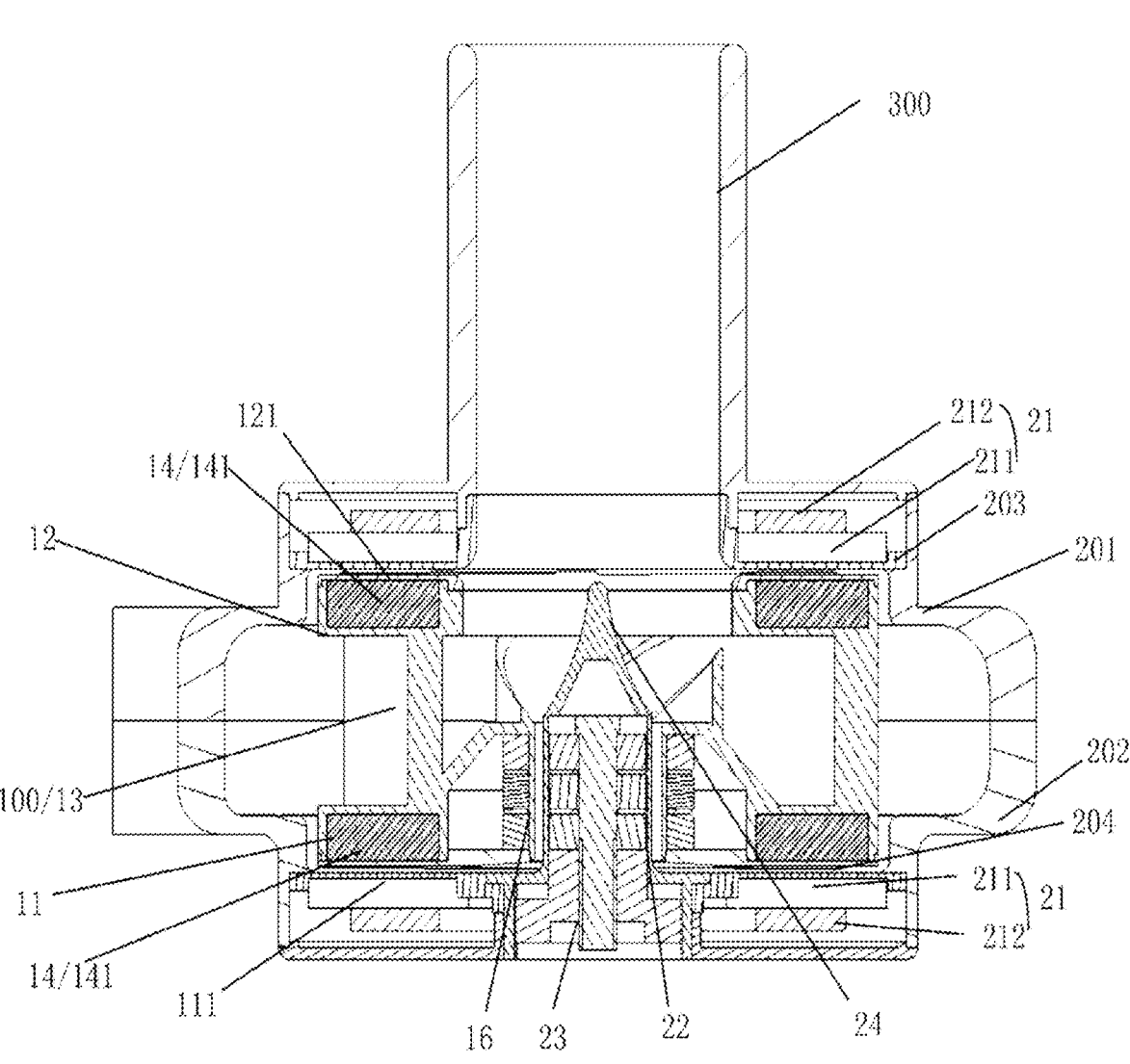
FIG. 3 is a schematic diagram of a cross-sectional structure of FIG. 1.

Please refer to FIGS. 1-3, FIG. 1 is a schematic diagram of a three-dimensional structure of a magnetic levitation centrifugal pump according to some embodiments of the present disclosure; FIG. 2 is a cross-sectional three-dimensional view of a magnetic levitation centrifugal pump; and FIG. 3 is a schematic diagram of a cross-sectional structure of FIG. 1.

Some embodiments of the present disclosure provide a magnetic levitation centrifugal pump, including a volute 200, a stator magnetic ring 22 and a rotor 100; the volute 200 is provided with a levitation cavity, a medium inlet and a medium outlet, and the rotor 100 is located inside the levitation cavity.

The volute 200 may include a first volute 201 and a second volute 202, wherein the first volute 201 and the second volute 202 enclose an installation space for the rotor, and the first volute 201 and the second volute 202 are able to be detachably installed, so as to facilitate installation and maintenance of components and parts such as the rotor. The first volute may be provided with the medium inlet, and the medium outlet may be enclosed by corresponding structures on the first volute and the second volute together. An inlet pipe is installed at the medium inlet, an outlet pipe is installed at the medium outlet, and the first volute, the second volute, the inlet pipe and the outlet pipe may all be made of a titanium alloy material.

Figure 4:
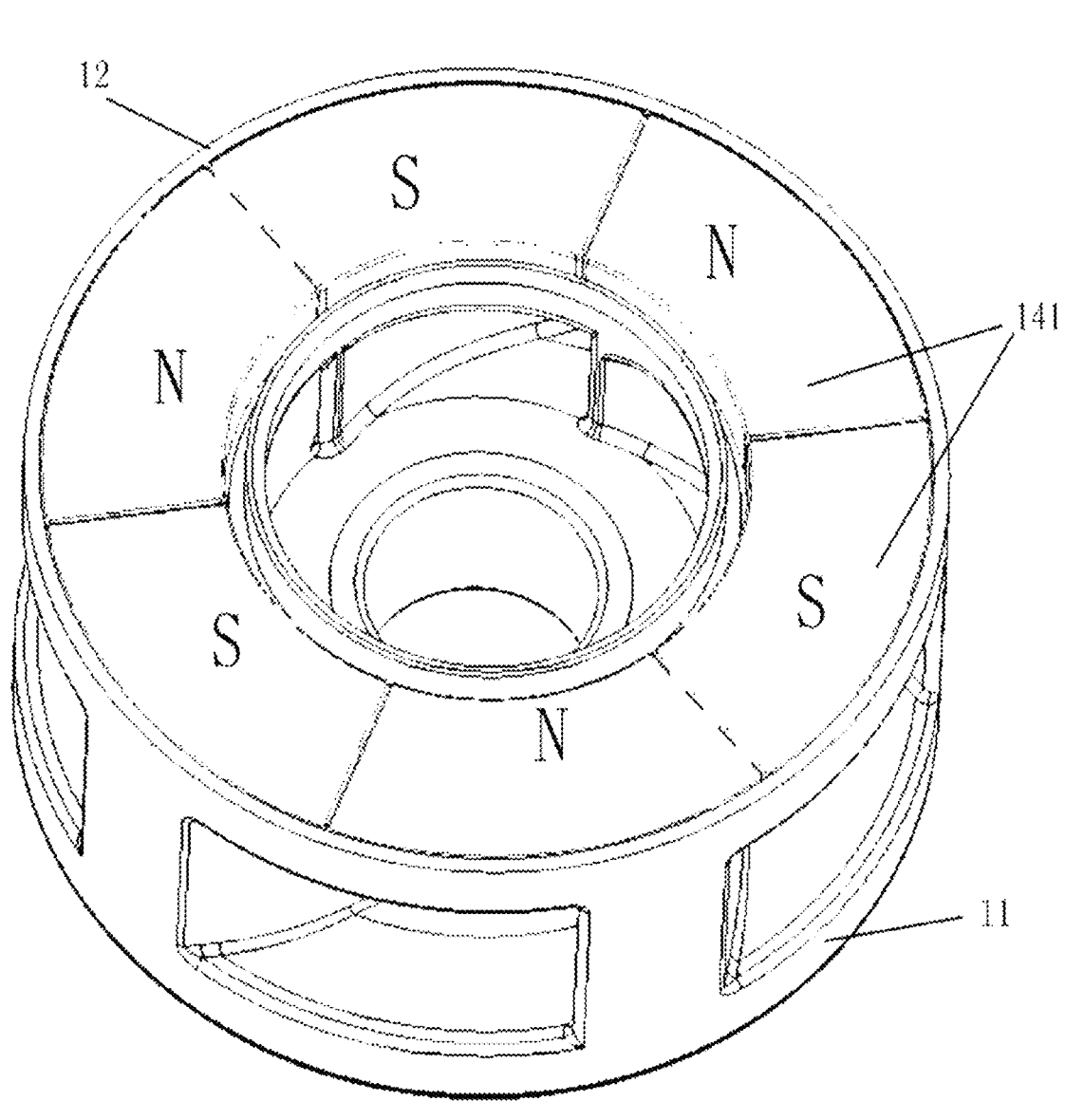
FIG. 4 is a schematic structural diagram of a rotor according to some embodiments of the present disclosure.
Figure 5:
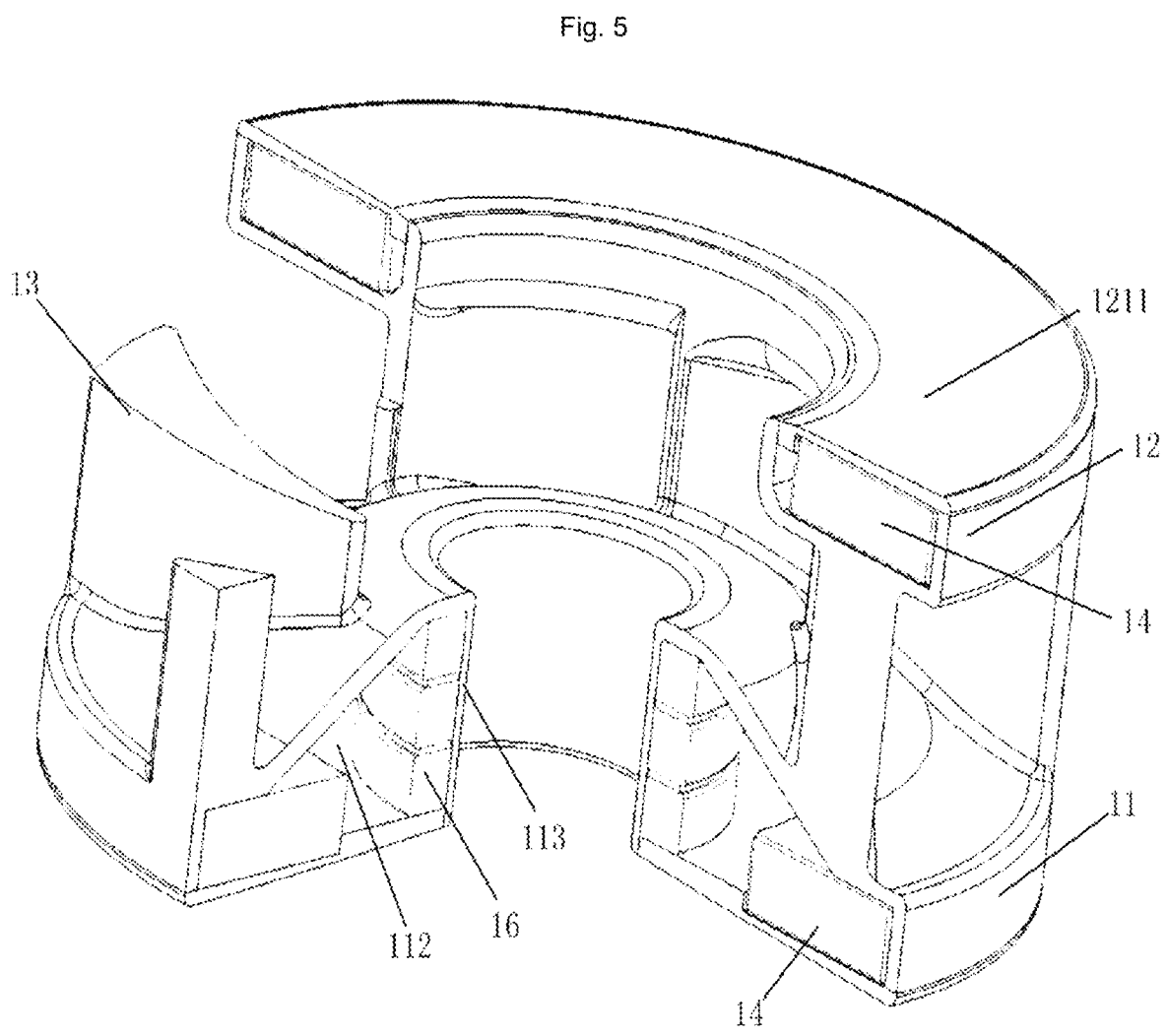
FIG. 5 is a schematic diagram of the rotor shown in FIG. 4 from another viewing angle.

Please further refer to FIGS. 4 and 5, FIG. 4 is a schematic structural diagram of a rotor according to some embodiments of the present disclosure; and FIG. 5 is a schematic diagram of the rotor shown in FIG. 4 from another viewing angle.

The rotor in some embodiments of the present disclosure includes a rotor body, blades 13, a dynamic magnetic ring 16, and a magnet steel assembly 14.

The rotor body mainly provides an installation base for an installation of other components and parts constituting the rotor, and is assembled in conjunction with the volute. Hereinafter, a specific structure of the rotor body will be described in detail. The dynamic magnetic ring, the blades and the magnet steel assembly are all installed on the rotor body. A number of the blades may be two or more, that is, the number of the blades is at least two. The blades are distributed along a circumferential direction, and the blades may be backward bent blades. For the backward bent blades, under the requirements of obtaining optimized fluid efficiency, shear force and streamline distribution and the requirements of the same output flow and pressure, diameters of the rotor and the volute are able to be smaller, and the requirements for a rotational speed and a torque of a motor are able to be lower, which is able to reduce the volumes of the volute, the rotor and the motor, and is able to achieve miniaturized pump under a condition of a same output capability, and reduce a possibility of hemolysis and thrombosis to the greatest extent.

The number of the blades may be determined according to the specific volume of the pump, and may generally be 3 to 7. For example, in a specific example, the number of the blades is 5.

Of course, the blades may also be blades of equal thickness or straight blades, as long as they are able to meet the use requirements.

The stator magnetic ring 22 is installed on the volute, and the stator magnetic ring and the dynamic magnetic ring 16 are coaxial with each other and are nested, to limit radial positions of the rotor and the volute. Both the stator magnetic ring and the dynamic magnetic ring may include two or more annular magnets arranged in an axial direction. FIG. 3 shows a specific example in which the stator magnetic ring and the dynamic magnetic ring each have three annular magnetic rings, wherein the dynamic magnetic ring is sleeved on an outer periphery of the stator magnetic ring. Certainly, a number of the annular magnetic rings in the stator magnetic ring and a number of the annular magnetic rings in the dynamic magnetic ring are not limited to those described herein, and may also be other values. As stated above, the rotor body is provided with a group of dynamic magnetic ring; the volute is provided with a group of stator magnetic ring; and the dynamic magnetic ring and the stator magnetic ring constitute a permanent magnet radial levitation bearing. An axial position of the stator magnetic ring is able to be adjusted by precise threads between the base and the volute, and a radial levitation of the rotor is realized by a repulsive force between the dynamic magnetic ring and the stator magnetic ring.

In the rotor body provided in some embodiments of the present disclosure, magnet steel assemblies 14 are fixed at both ends of the rotor body, each magnet steel assembly includes N first magnet steels 141 arranged along the circumferential direction, and magnetic poles of all the first magnet steels are arranged alternately. Please refer to FIG. 4, first magnet steels in each magnet steel assembly are arranged alternately according to N poles and S poles to form a circle. Magnet steels in the magnet steel assembly are able to be encapsulated inside the rotor body. In an example, the first magnet steels may be closely attached to each other to form a magnetic ring with a full pole arc, such that disc-type motors formed by the magnet steel assemblies and driving coil assemblies installed on the volute may obtain relatively high motor efficiency.

Of course, the magnet steel assembly may further include transverse magnetic conductive magnet steels 18, the magnetic conductive magnet steels 18 being located between the first magnet steels; that is, a same number of mutually-exclusive transverse magnetic conductive magnet steels are arranged between the first magnet steels of which the magnetic poles are staggered. For example, 10 groups of staggered first magnet steels and magnetic conductive magnet steels constitute a Halbach magnet steel array (the group number may be even number, e.g. 4-16, and the group number being 10 is an optional solution). Such a magnet steel array is able to achieve a magnetism gathering effect, and improves the magnetic density between air gaps of the motor under the same volume of magnet steel, thereby further increasing the motor efficiency.

Definitely, the arrangement of the magnet steel assemblies is not limited to the methods described herein, and may also be other methods, as long as the functions described herein are able to be implemented.

Correspondingly, driving coil assemblies 21 are encapsulated at corresponding ends, where the magnet steel assemblies are installed, of the volute and the rotor, wherein each of the driving coil assemblies may include a driving coil 211 and a working iron core 212. The driving coil assemblies at the two ends may be arranged symmetrically with respect to a central cross section of the levitation cavity, and certainly may also be arranged asymmetrically. During operation, an alternating current is introduced into the driving coil to generate a magnetic field, and the working iron core serves a function of amplifying the magnetic field generated by the driving coil; and the first magnet steels, of which the magnetic poles are arranged alternately, of the magnet steel assembly installed on the rotor body will generate an axial force. A controller confirms the difference between the positions of the rotor from an upper driving coil and a lower driving coil by detecting the difference in electromotive force or inductance fed back by the upper driving coil and the lower driving coil. In this way, by adjusting driving parameters (not limited to current, voltage, duty ratio, etc.) of the upper and lower driving coils, a magnitude of the axial force generated by the driving coils on the first magnet steels in the rotor is changed, thereby controlling an axial position of the rotor, such that the rotor body is always balanced at a central position having equal distances from upper and lower end walls of the volute under an action of an axial electromagnetic force of the motor and is in levitation operation.

Since no additional coil and sensor assembly is required in such a levitation manner, the volume and weight are able to be greatly reduced; the control of the position of the rotor body is realized by adjusting the currents of the upper and lower motors, and thus no additional power consumption is generated due to the position control; and since a sensor assembly is not required for axial position control, a centrifugal pump implanted into the body has no electronic device, has a stronger anti-interference capability, higher reliability, and does not decrease in performance with an increase of working time. Therefore, compared with the related art, this axial levitation technique is able to achieve high reliability and miniaturization of the blood pump.

In addition, in some embodiments of the present disclosure, full levitation operation of the rotor is able to be realized by the magnetic action between the dynamic magnetic ring and the stator magnetic ring; in this way, there is no mechanical contact between the rotor and the volute (equivalent to a stator), thereby reducing the heat generated and wear, and maximally reducing a possibility of thrombus generation and crushing damage to blood cells. A radial levitation limit of the rotor is able to be realized by the dynamic magnetic ring and the stator magnetic ring.

Figure 8:
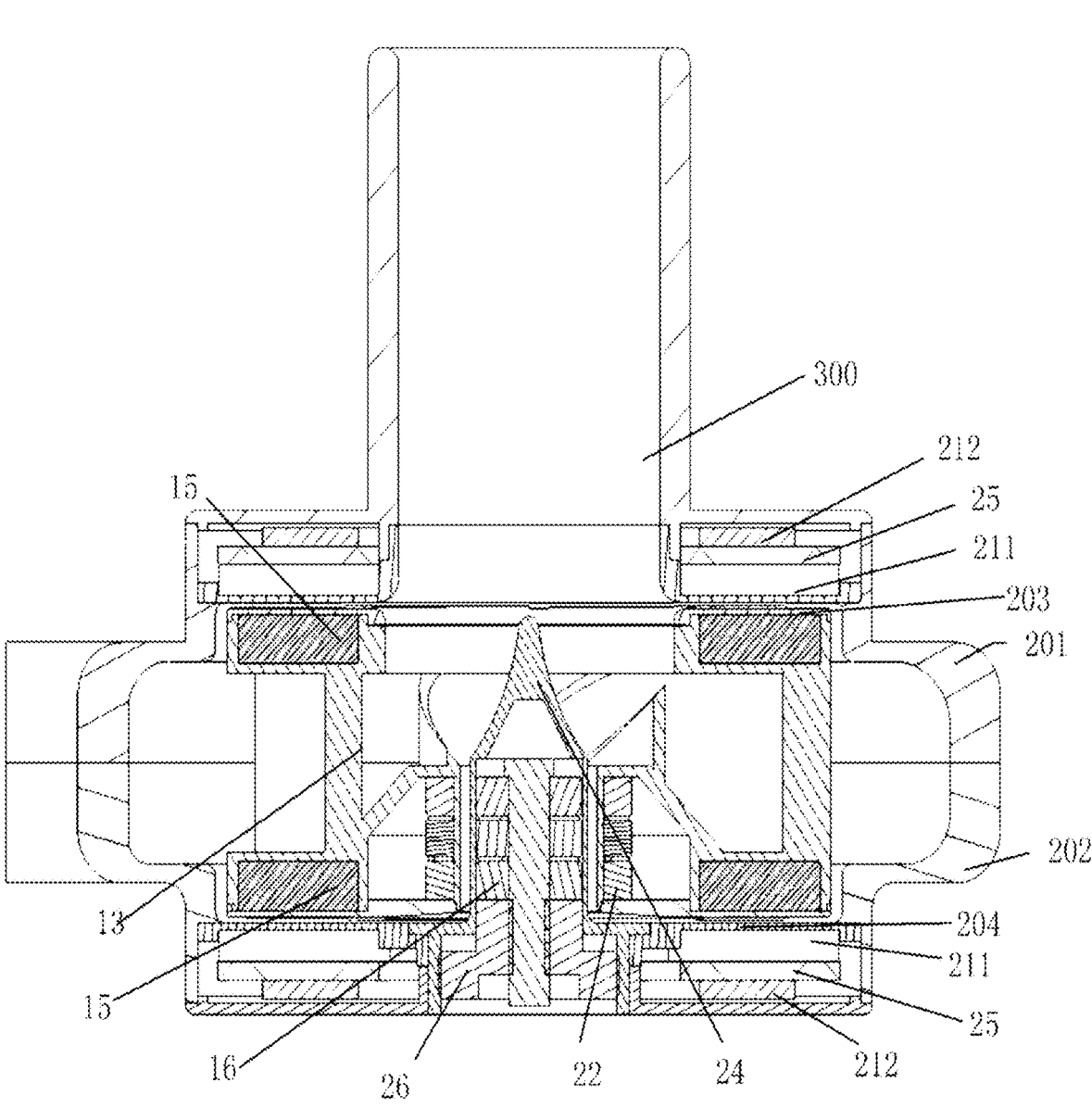
FIG. 8 is a cross-sectional schematic diagram of a magnetic levitation centrifugal pump according to a second embodiment of the present disclosure.
Figure 9:
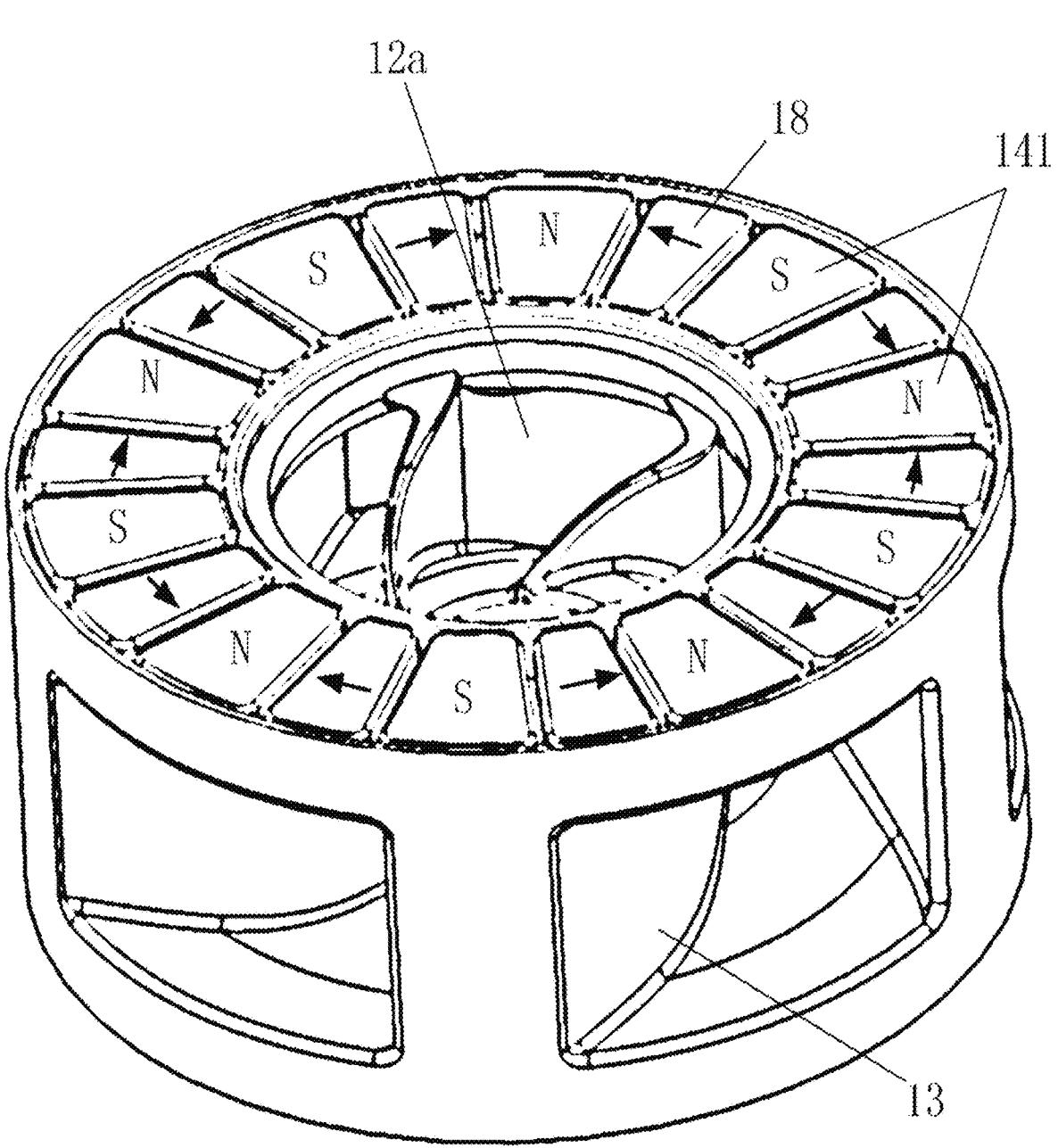
FIG. 9 is a three-dimensional view of the rotor as shown in FIG. 8 of the present disclosure.

Please refer to FIGS. 8 and 9, FIG. 8 is a cross-sectional schematic diagram of a magnetic levitation centrifugal pump according to a second embodiment of the present disclosure; and FIG. 9 is a schematic three-dimensional view of the rotor of FIG. 8 according to some embodiments of the present disclosure.

In order to simplify the control logic, in some embodiments of the present disclosure, at least one end of the rotor body is also encapsulated with a magnetic component 15, and the accompanying drawings show specific examples in which both ends of the rotor body are encapsulated with magnetic components. The magnetic component may be at least one of an iron core or a second magnet steel. Corresponding ends of the volute are also encapsulated with magnetic levitation coils 25, and when a direct current is introduced to the magnetic levitation coils, the magnetic levitation coils generate an axial force with the magnetic components.

When the two ends of the rotor body are both encapsulated with the magnetic components, the two magnetic components are able to be symmetrical with respect to the central cross section of the rotor body; and the two ends of the volute are both encapsulated with the magnetic levitation coils, the two magnetic levitation coils are symmetrical with respect to the central cross section of the levitation cavity, and the symmetrical arrangement facilitates control.

In this way, a rotation of the rotor body is able to be realized by controlling the currents of the driving coils, and an adjustment of the axial position of the rotor body is able to be realized by controlling the currents of the magnetic levitation coils.

In a specific example, there may be a plurality of magnetic components evenly arranged along the axial direction, and the magnetic components are arranged between adjacent first magnet steels. FIG. 9 shows a specific embodiment in which the magnetic components and the first magnet steels are arranged alternately. The magnetic levitation centrifugal pump of this embodiment has a compact structure.

Of course, the magnetic components and the first magnet steels may also be stacked in the axial direction.

In this specific example, an inner cavity of the volute is provided with annular housings, sealed cavities are enclosed by the annular housings and the volute, and the driving coil assemblies are located in the sealed cavities; and of course, in the embodiments above having the magnetic levitation coils, the magnetic levitation coils are also located in the sealed cavities. The levitation cavities is formed between two annular housings at two ends. Herein, an annular housing installed on the first volute is defined as a first annular housing 203, and an annular housing installed on the second volute is defined as a second annular housing 204. That is to say, the rotor body is able to axially reciprocate between the two annular housings. The two annular housings are of ceramic structures.

The annular housings may be adhered to or otherwise fixed to the volutes.

The ceramic material has good compatibility with blood, and the ceramic material is very hard and insulating. In this way, a wall thickness of the annular housings is able to be relatively thin, and the driving coils are able to be tightly attached to the inner wall, thereby greatly reducing the air gaps between the driving coils and the first magnet steels, and completely eliminating an eddy loss. The first magnet steels are able to be arranged in an Halbach array, thereby increasing the efficiency of the motor, and realizing the miniaturization of the blood pump on the premise of keeping the maximum output capability unchanged. Due to the insulation property of the ceramic, a risk of the driving coils generating a leakage current for blood flowing in the volute is able to be reduced to the maximum extent, and the possibility that operation of the disc-type motors formed by the driving coil assemblies and the first magnet steel assembly is interfered by an external electric field is eliminated. For example, when a patient receives electric shock/electrical cardioversion/electric scalpel cutting treatment, the magnetic levitation centrifugal pump is still able to operate normally.

Figure 6:
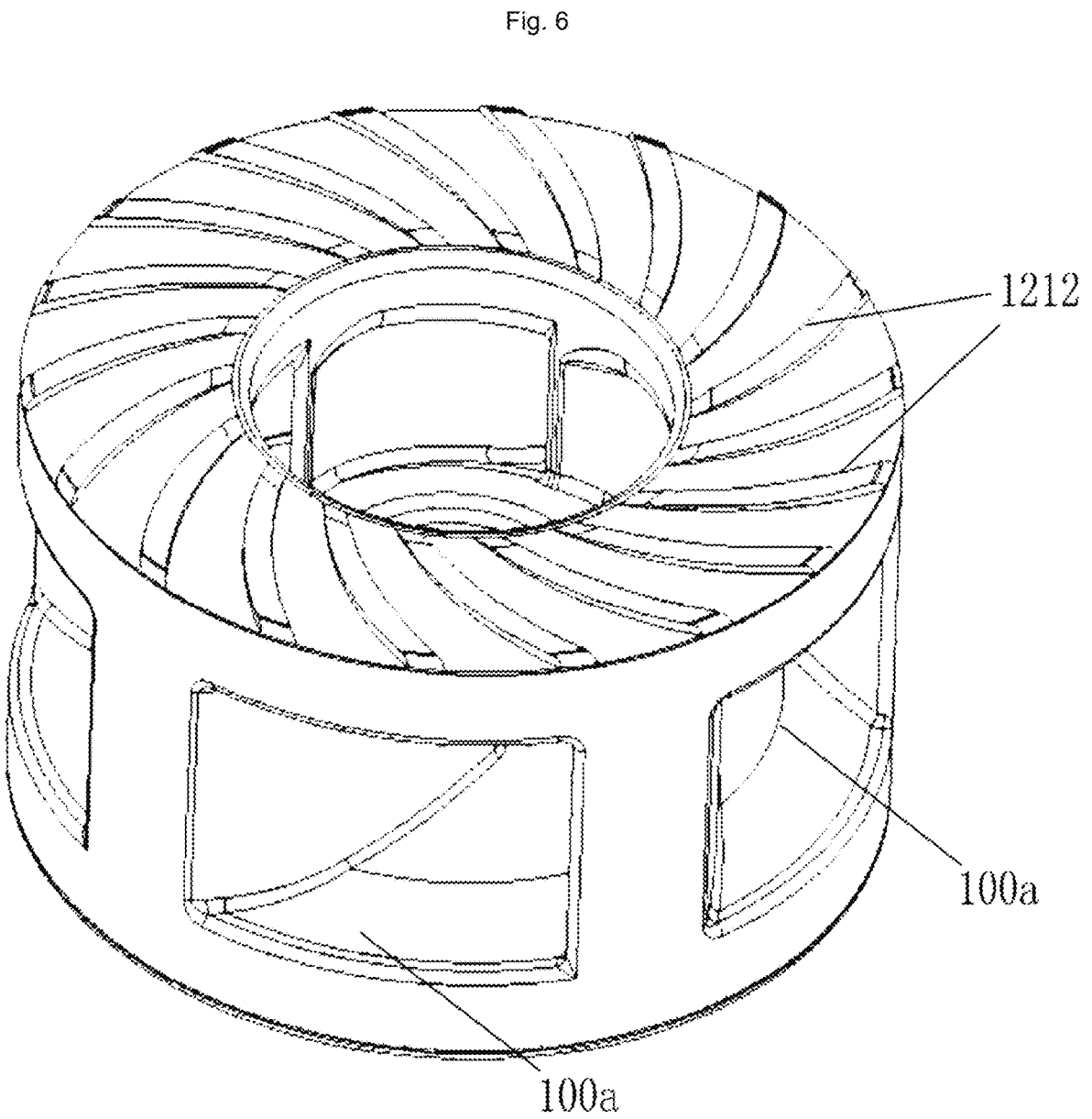
FIG. 6 is a schematic diagram of a rotor in some other embodiments of the present disclosure.
Figure 7:
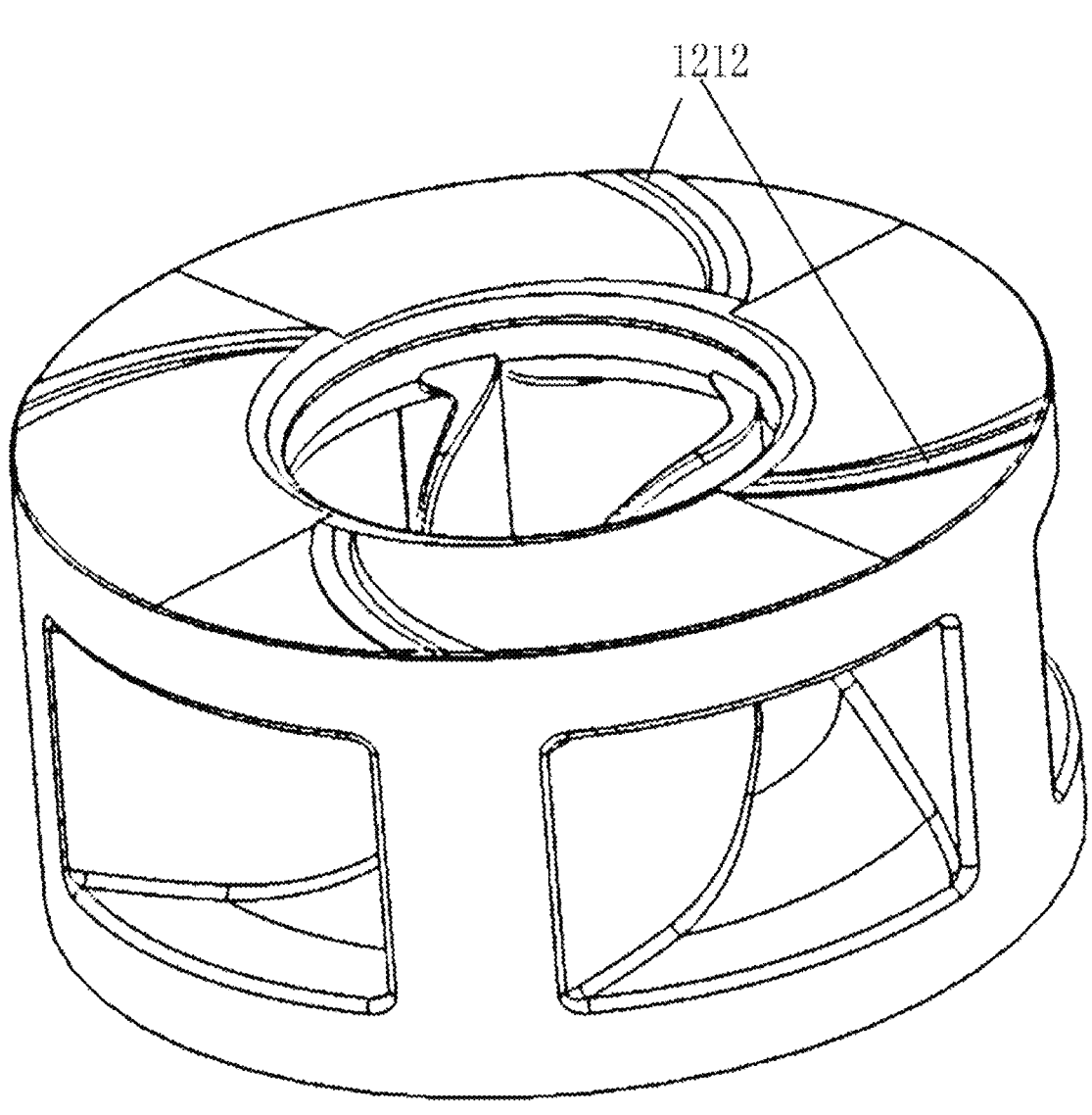
FIG. 7 is a schematic diagram of a rotor in still some other embodiments of the present disclosure.

Please refer to FIGS. 6 and 7, FIG. 6 is a schematic diagram of a rotor in some other embodiments of the present disclosure; and FIG. 7 is a schematic diagram of a rotor in still some other embodiments of the present disclosure.

In an example, the rotor body includes an annular body 12 and a base body 11, which are fixedly connected with each other in the axial direction; liquid outlets 100a are provided between the annular body 12 and the base body 11, a central through-hole of the annular body 12 is in communication with the liquid outlets; various blades are located between the annular body 12 and the base body 11, magnet steel assemblies are encapsulated in both the annular body 12 and the base body 11, and the dynamic magnetic ring is encapsulated inside the base body 11. The annular body 12 and the base body 11 are fixedly connected with each other in the axial direction, liquid outlets are provided between the annular body 12 and the base body 11, a central through-hole of the annular body 12 is in communication with the liquid outlets; the central through-hole of the annular body 12 is coaxial with the medium inlet, the number of the liquid outlets may be multiple, and the liquid outlets are uniformly arranged in a circumferential direction, and the specific number of the liquid outlets may be determined according to specific products, and is not limited herein.

In some embodiments, the base body 11 has a first annular encapsulating cavity 112, the dynamic magnetic ring is sleeved in an inner ring wall of the first annular encapsulating cavity, the first iron cores and the magnet steel assemblies encapsulated in the base body 11 are located on a periphery of the dynamic magnetic ring; and along a radial direction, an axial height of a middle region of the first annular encapsulating cavity is greater than an axial height of an edge region of the first annular encapsulating cavity.

In this way, the space occupied by the encapsulating cavity for the internal fluid space of the pump is able to be reduced as far as possible, facilitating the formation of a compact structure.

To facilitate installation, the first annular encapsulating cavity may be formed in the following manner: an annular groove is provided on the base body 11, and a lower cover plate 111 covers a groove opening of the annular groove to form a sealed chamber. By the same reasoning, the sealed cavity for installation of the magnet steel assembly on the annular body 12 may also be formed by arranging the annular groove and the upper cover plate 121 which cooperate to achieve sealing.

The rotor in some embodiments of the present disclosure may be a centrifugal fully-enclosed rotor. When the centrifugal pump operates, a large amount of blood flows into the centrifugal pump through an inflow channel, and after being accelerated by centrifugal blades of the rotor, the blood flows out of an outflow channel, and the blood is injected into an aorta, thereby providing pressure and flow for the systematic blood circulation. The centrifugal blades of the rotor are of a hollow structure.

Figure 10:
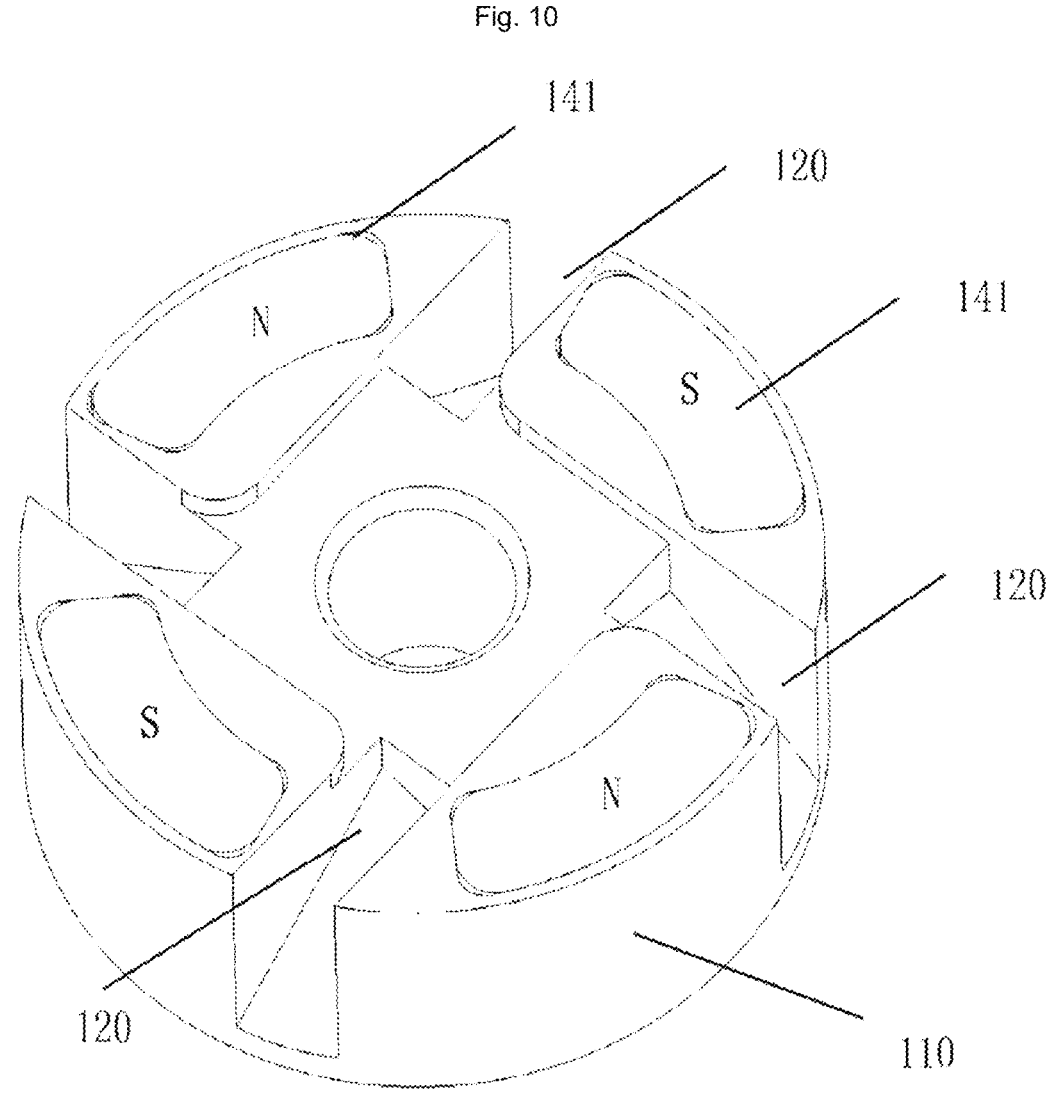
FIG. 10 is a schematic diagram of a rotor in still some other embodiments of the present disclosure.
Figure 11:
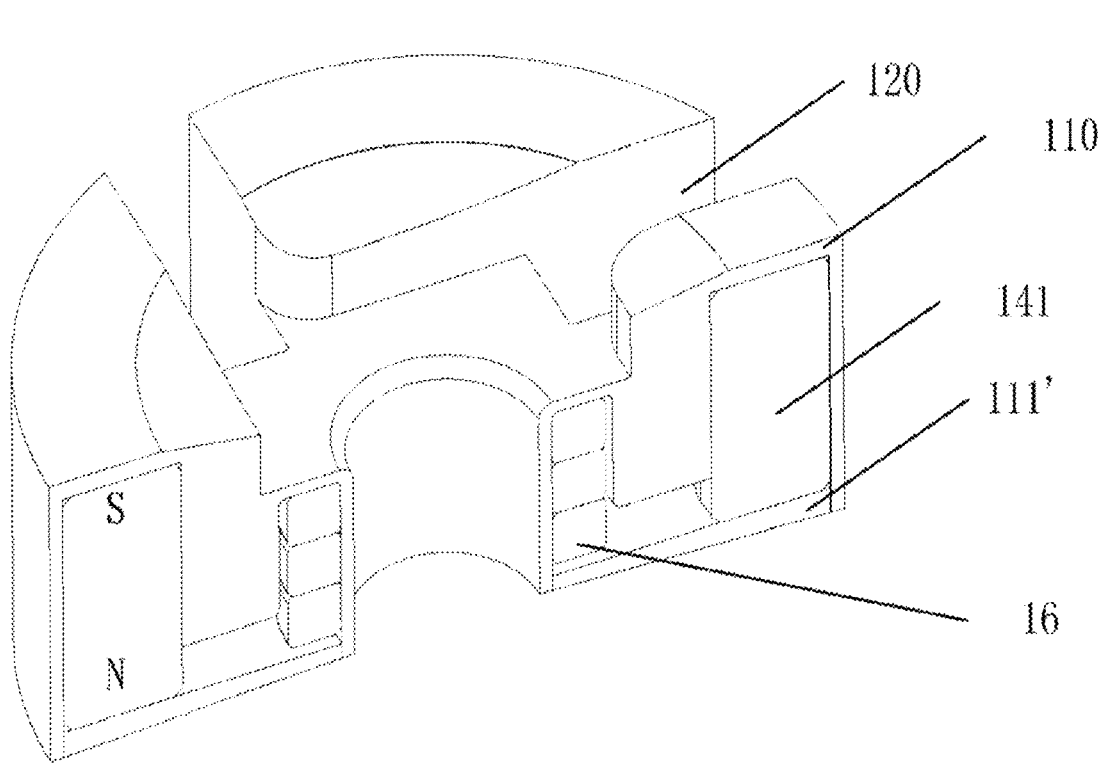
FIG. 11 is a partial cross-sectional view of the rotor as shown in FIG. 10.

Please refer to FIGS. 10 and 11, in some other specific embodiments, a rotor body 100' includes an annular housing 110; the number of the magnet steel assembly 14 may be one, and each first magnet steel 141 is encapsulated in an inner cavity of the annular housing 110, and the each first magnet steel 141 extends from one end of the rotor body to the other end, and N poles and S poles of the each first magnet steel 141 are respectively close to two ends of the annular housing 110. An end face of the annular housing 110 facing towards the medium inlet of the volute is further provided with at least two groove bodies 120, and openings of the groove bodies 120 face towards the medium inlet of the volute, the groove bodies 120 are located between adjacent first magnet steels, and the groove bodies 120 form main liquid flow channels of the rotor body. That is to say, in this embodiment, medium entering from the medium inlet of the volute flows out from the groove bodies 120 to flow to the medium outlet, and the rotor 100' may be a centrifugal semi-closed rotor structure. The installation of the dynamic magnetic ring 16 in the rotor may be the same as that in the described embodiments.

The stator magnetic ring in the described embodiments may be installed inside the volute in the following methods.

In an example, the magnetic levitation centrifugal pump may further include a base and a cover body snap-fitted to the base, wherein the cover body is hermetically fixed to the base, the stator magnetic ring is fixed to the base by a threaded component, and the threaded component may be components such as screws, bolts, threaded rods or the like. Furthermore, the stator magnetic ring is installed in an installation space formed by the cover body and the base, a second end of the volute is provided with an installation through-hole, the installation through-hole is coaxial with the medium inlet, and the base is in a threaded and sealed connection with the installation through-hole. The cover body includes a cylinder provided with an opening at one end and a flow guide cone 24 connected with the other end of the cylinder, the stator magnetic ring is located inside the cylinder, and the flow guide cone passes through a central hole of the base body 11 and protrudes towards the medium inlet. The closer the flow guide cone is to the medium inlet, the smaller the radial dimension of the flow guide cone is, such that fluid at the medium inlet of the volute is able to flow uniformly in the circumferential direction under diversion of the flow guide cone, and then enter uniformly between the blades.

In the foregoing embodiments, the base 23 is in threaded connection with the volute, such that the axial position of the base relative to the volute is able to be precisely adjusted, so as to precisely match the dynamic magnetic ring on the rotor.

Please refer to FIG. 9, in each of the foregoing embodiments, an outer end face 1211 of the annular body 12 and an outer end face (having no reference sign) of the base body 11 are both provided with a plurality of protrusions 1212. Each of the protrusions extends from an inner edge side to an outer edge side, and have a predetermined included angle with a radial direction. The closer to the inner edge side, the smaller a distance between adjacent protrusions, and the protrusions have an inner spiral structure. In this way, hydrodynamic fluid floating bearings are formed between an outer end face of the annular body 12 and an upper annular housing, and between an outer end face of the base body 11 and a lower annular housing. When the rotor is greatly interfered in the axial direction and one end is approaching the annular housing at the side, the hydrodynamic fluid floating bearings are able to provide an additional restoration force to the center, thereby improving the stability of an impeller in the axial direction.

Please refer to FIG. 10, certainly, the closer to the inner edge, the lower a height of each of the plurality of protrusions, which is also able to achieve the same technical effect as above.

In some specific embodiments, a first auxiliary channel is formed between an outer peripheral wall and an outer end wall of the annular body 12 and a corresponding inner wall of the volute; and a second auxiliary channel is formed between an outer peripheral wall and an outer end wall of the first annular encapsulating cavity and a corresponding inner wall of the volute, and between an inner peripheral wall 113 of the first annular encapsulating cavity and the cover body.

During operation, the rotor levitates and rotates at a high speed in the middle of the volute; the blades between the annular body 12 and the base body 11 and the inner wall of the volute constitute a main flow channel of the pump; blood flows in from the medium inlet, enters the main flow channel between the blades through the central through-hole of the annular body 12, and after being accelerated by the rotation of the blades, the blood enters the main flow channel inside the volute, and flows out of the volute through the medium outlet.

Moreover, a small portion of the blood entering the main flow channel inside the volute reflows back to the inlet of the rotor body through the first auxiliary channel 1a and the second auxiliary channel 1b, respectively, and reenters between the blades and flows into the volute after being accelerated. By the described design, all the flow channels through which the blood flows and enters the centrifugal pump involve unidirectional flowing, and there is no static or reflowing region, thereby reducing the possibility of thrombus formation to the greatest extent.

In addition, as described above, as the annular housings opposite to the end faces of the annular body 12 and the base body 11 are made of a ceramic material, the surface of the ceramic is hard and smooth, and when the rotor accidentally contacts the annular housings, the possibility of the surfaces of the annular housings being damaged is reduced. The motor has high efficiency, and thus under the same condition, a thickness of the first magnet steels in the rotor is able to be thinner, and a thickness of the outer end walls (the cover plates) of the annular body 12 and the base body 11 is also correspondingly thinned, thereby reducing a length of a reflow channel in the volute.

Moreover, the outer end face of the annular body 12 and the outer end face of the base body 11 both have a predetermined included angle with a horizontal plane, and from outside to inside, a distance between the outer end face and the horizontal plane increases. That is, the outer end faces of the annular body 12 and the base body 11 are recessed inwards, and the upper and lower outer end faces of the rotor are provided with inward tapered faces. Therefore, the auxiliary channel formed between the outer end face and the inner wall of the volute has a relatively small gap on the outer side, and a relatively large gap on the inner side. In this way, when the blood passes through the outer-side gap with a relatively small region, the shear force is high but the flow rate is high and the passing time is short; and when the blood passes through the inner-side gap with a relatively large region, the flow rate is relatively low but the shear force is also low, thereby minimizing the possibility of hemolysis and thrombosis. Thus, it is possible to reduce the gap of the auxiliary channel, thereby reducing the reflow loss of the centrifugal pump, and increasing the fluid efficiency. Under the requirements of the same output flow/pressure of the centrifugal pump, the diameters of the rotor and the volute are able to be smaller, and the requirements for the rotational speed and torque of the motor are able to be lower, thereby reducing the volume of the volute/the rotor, and realizing the miniaturization of the centrifugal pump under the same output capability.

Hereinabove, a magnetic levitation centrifugal pump provided in some embodiments of the present disclosure has been described in detail. The principle and embodiments of the present disclosure are described herein by applying specific examples, and the illustration of the embodiments above is only used to help understand the method and core ideas of some embodiments of the present disclosure. It should be noted that, a person of ordinary skill in the art may further make several improvements and modifications to some embodiments of the present disclosure without departing from the principle of some embodiments of the present disclosure, and these improvements and modifications also belong to the scope of protection of the claims of the present disclosure.

What is claimed is:

1. A magnetic levitation centrifugal pump, comprising a volute, a stator magnetic ring and a rotor; the volute is provided with a levitation cavity, a medium inlet and a medium outlet, the rotor is located inside the levitation cavity, and the stator magnetic ring is fixed to the volute; the rotor comprises a rotor body and a dynamic magnetic ring positioned on the rotor body;

the dynamic magnetic ring and the stator magnetic ring are coaxial with each other and are nested, to limit radial positions of the rotor body and the volute; a magnet steel assembly is further fixed at the rotor body, the magnet steel assembly comprises N first magnet steels arranged along a circumferential direction, and magnetic poles of all the first magnet steels are arranged alternately;

two ends of the volute are encapsulated with driving coil assemblies, and two driving coil assemblies cooperate with the magnet steel assembly to provide an axial force for the rotor body to move in an axial direction and a rotational force;

wherein two ends of the rotor body are both provided with the magnet steel assemblies, and the magnet steel assemblies at the two ends of the rotor body are symmetrical with respect to a central cross section of the rotor body;

the driving coil assemblies located at the two ends of the volute are symmetrical with respect to a central cross section of the levitation cavity;

one of the magnet steel assemblies and one of the two driving coil assemblies at a same side form a disc-type motor, and disc-type motors at the two ends jointly provide the axial force for the rotor body to move in the axial direction and the rotational force; or adjacent first magnet steels are attached, the magnet steel assembly further comprises transverse magnetic conductive magnet steels, the magnetic conductive magnet steels being located between two first magnet steels, and all the magnetic conductive magnet steels and all the first magnet steels form an Halbach magnet steel array, wherein the rotor body comprises an annular body and a base body, which are fixedly connected with each other in the axial direction; liquid outlets are provided between the annular body and the base body, a central through-hole of the annular body is in communication with the liquid outlets; the central through-hole is coaxial with the medium inlet, blades are provided between the annular body and the base body to form a fully-enclosed rotor structure, and the magnet steel assemblies are encapsulated in both the annular body and the base body, and the dynamic magnetic ring is encapsulated inside the base body; and wherein a first auxiliary channel is formed between an outer peripheral wall and an outer end wall of the annular body and a corresponding inner wall of the volute; and a second auxiliary channel is formed between an outer peripheral wall and an outer end wall of the first annular encapsulating cavity and a corresponding inner wall of the volute, and between an inner peripheral wall of the first annular encapsulating cavity and the cover body; moreover, an outer end face of the annular body and an outer end face of the base body both have a predetermined included angle with a horizontal plane, and from outside to inside, a distance between the outer end face and the horizontal plane increases.

2. The magnetic levitation centrifugal pump according to claim 1, wherein at least one end of the rotor body is also encapsulated with a magnetic component, a corresponding end of the volute is also encapsulated with a magnetic levitation coil, and when the magnetic levitation coil is energized, the magnetic levitation coil and the magnetic component generate an axial force; wherein the magnetic component comprises at least one of an iron core or a second magnet steel.

3. The magnetic levitation centrifugal pump according to claim 2, wherein two ends of the rotor body are both encapsulated with the magnetic components, and two magnetic components are able to be symmetrical with respect to a central cross section of the rotor body; and the two ends of the volute are both encapsulated with the magnetic levitation coils, and two magnetic levitation coils are symmetrical with respect to a central cross section of the levitation cavity.

4. The magnetic levitation centrifugal pump according to claim 2, wherein there are a plurality of magnetic components evenly arranged along the circumferential direction, and each of the plurality of magnetic components is arranged between adjacent first magnet steels; or/and, the plurality of magnetic components and the first magnet steels are stacked in the axial direction; or/and, the plurality of magnetic levitation coils and the driving coil assemblies are stacked in the axial direction.

5. The magnetic levitation centrifugal pump according to claim 1, wherein the base body is provided with a first annular encapsulating cavity, the dynamic magnetic ring is sleeved in an inner ring wall of the first annular encapsulating cavity, first iron cores and the magnet steel assemblies encapsulated in the base body are located on a periphery of the dynamic magnetic ring; and along a radial direction, an axial height of a middle region of the first annular encapsulating cavity is greater than an axial height of an edge region of the first annular encapsulating cavity.

6. The magnetic levitation centrifugal pump according to claim 5, wherein the centrifugal pump further comprises a base and a cover body, the cover body comprises a cylinder provided with an opening at one end and a flow guide cone connected with the other end of the cylinder, and the opening of the cylinder is circumferentially sealed and fastened to the base; the stator magnetic ring is fixed to the base by a threaded component and located inside the cylinder, and the base is in a threaded and sealed connection with the volute and coaxial with the medium inlet, and the flow guide cone passes through a central hole of the first annular encapsulating cavity and protrudes towards the medium inlet.

7. The magnetic levitation centrifugal pump according to claim 1, wherein an outer end face of the annular body and an outer end face of the base body are both provided with a plurality of protrusions; each of the plurality of protrusions extends from an inner edge side to an outer edge side, and have a predetermined included angle with a radial direction, wherein a spacing between adjacent protrusions decreases in a direction from the outer edge toward the inner edge, or wherein a height of the protrusions decreases in a radial direction toward the inner edge, or, the blades are backward bent blades.

8. The magnetic levitation centrifugal pump according to claim 1, wherein the rotor body is an annular housing, a number of the magnet steel assembly is one, and each of the first magnet steels is encapsulated in an inner cavity of the annular housing, and each of the first magnet steels extends from one end of the rotor body to the other end; an end face of the annular housing facing towards the medium inlet of the volute is further provided with at least two groove bodies, and openings of the groove bodies face towards the medium inlet of the volute, each of the groove bodies is located between adjacent first magnet steels, and the groove bodies form main liquid flow channels of the rotor body.

9. The magnetic levitation centrifugal pump according to claim 1, wherein at least one end of the rotor body is also encapsulated with a magnetic component, corresponding end of the volute is also encapsulated with a magnetic levitation coil, and when the magnetic levitation coil is energized, the magnetic levitation coil and the magnetic component generate an axial force; wherein the magnetic component comprises at least one of an iron core and a second magnet steel.

10. The magnetic levitation centrifugal pump according to claim 1, wherein an inner cavity of the volute is provided with annular housings, sealed cavities are enclosed by the annular housings and the volute, and the driving coil assemblies are located in the sealed cavities; and the levitation cavity is formed between two annular housings at two ends, the two annular housings are of ceramic structures, and the driving coil assemblies are arranged abutting against the annular housings.

11. The magnetic levitation centrifugal pump according to claim 9, wherein the two ends of the rotor body are both encapsulated with the magnetic components, and two magnetic components are able to be symmetrical with respect to a central cross section of the rotor body; and the two ends of the volute are both encapsulated with the magnetic levitation coils, and two magnetic levitation coils are symmetrical with respect to a central cross section of the levitation cavity.

* * * * *